Figure 1:
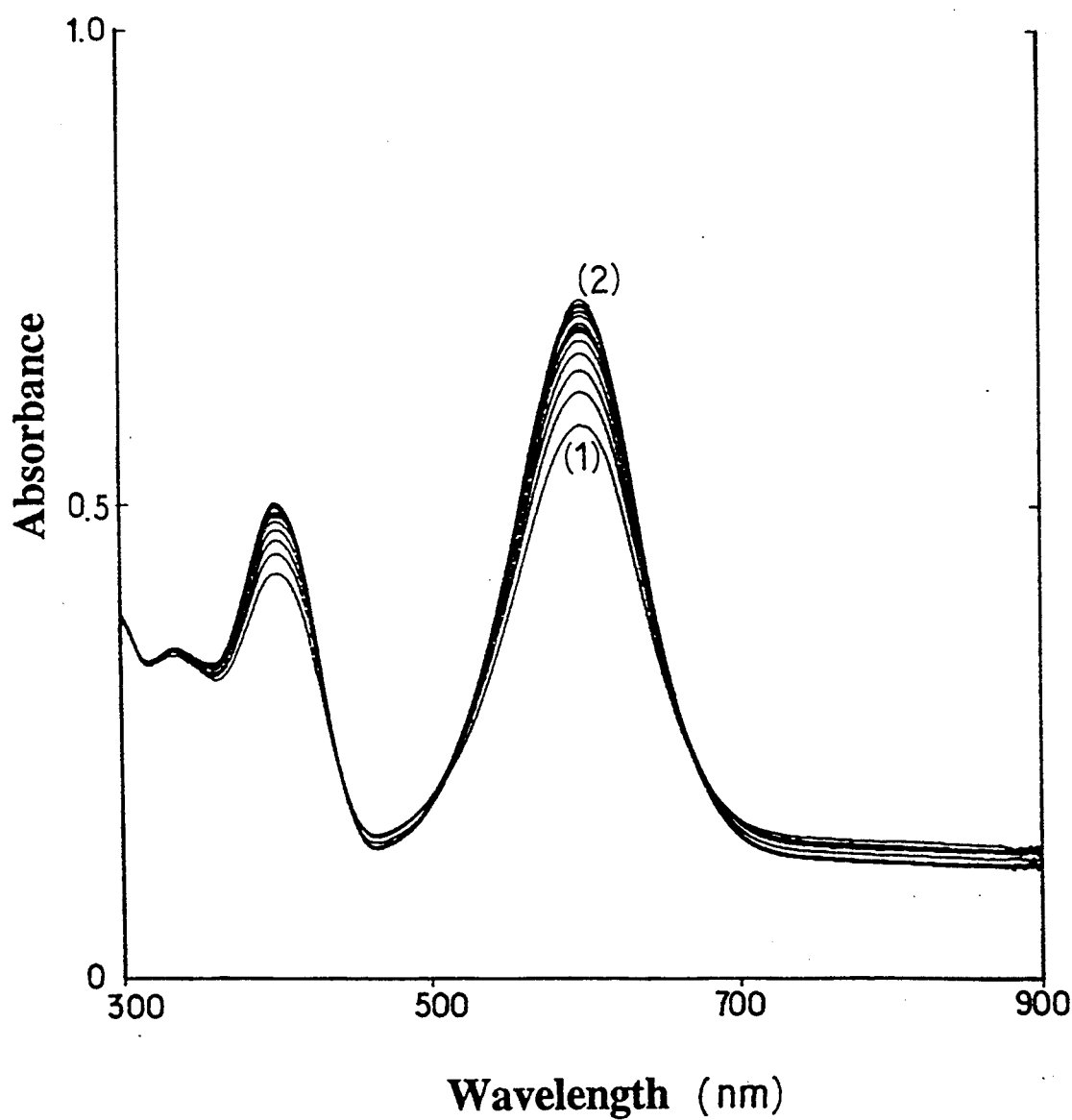

United States Patent

Miyashita

[11] Patent Number: 5,236,958
[45] Date of Patent: Aug. 17, 1993

[54] BENZOSELENAZOLINO-VINYLSPIROPYRAN COMPOUND

[75] Inventor: Akira Miyashita, Ageo, Japan

[73] Assignee: Otsuka Kagaku Kabushiki Kaisha, Osaka, Japan

[21] Appl. No.: 768,681

[22] PCT Filed: Feb. 18, 1991

[86] PCT No.: PCT/JP91/00202
§ 371 Date: Oct. 17, 1991
§ 102(e) Date: Oct. 17, 1991

[87] PCT Pub. No.: WO91/13072
PCT Pub. Date: Sep. 5, 1991

[30] Foreign Application Priority Data

Feb. 23, 1990 [JP] Japan .................. 2-44073
Feb. 26, 1990 [JP] Japan .................. 2-46990

[51] Int. Cl.⁵ ............................ C07D 293/12
[52] U.S. Cl. ............................ 518/121
[58] Field of Search ..................... 548/121

[56] References Cited

U.S. PATENT DOCUMENTS 4,197,124  4/1980  Ikeda ................... 430/302

FOREIGN PATENT DOCUMENTS 59-227972 12/1984 Japan .
61-76490   4/1986 Japan ................... 548/121
61-76514   4/1986 Japan ................... 548/121
2-78685    3/1990 Japan .
WO90/10007 9/1990 World Int. Prop. O. .

Primary Examiner—Robert Gerstl
Attorney, Agent, or Firm—Armstrong, Westerman, Hattori, McLeland & Naughton

[57] ABSTRACT

The present invention provides a photochromic compound of the formula (Ia)

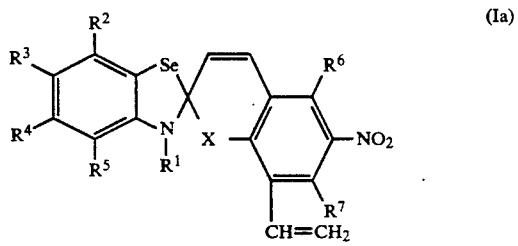

wherein $R^1$ is a $C_1$-$C_{20}$ alkyl group or an aralkyl group; $R^2$, $R^3$, $R^4$ and $R^5$ each represents H, a $C_1$-$C_6$ alkyl group, an aryl group, an aralkyl group, a $C_1$-$C_5$ alkoxy group, a halogen atom, a cyano group, a trichloromethyl group, a trifluoromethyl group or a nitro group; $R^6$ and $R^7$ each represents H, a $C_1$-$C_6$ alkyl group, an aryl group, an aralkyl group, a halogen atom, a cyano group or a nitro group; and X is an oxygen atom or a sulfur atom, and a homopolymer of the above compound or a copolymer of the above compound and a vinyl compound represented by the formula $$CH_2=C(Y)(Z)$$

wherein Y is H or $CH_3$; and Z is a carboxyl group, an alkoxy-carbonyl group, a cyano group, a carbamoyl group, an N,N-dimethylcarbamoyl group, an acetoxy group, a phenyl group or a methylphenyl group.

4 Claims, 5 Drawing Sheets

BENZOSELENAZOLINO-VINYLSPIROPYRAN COMPOUND

TECHNICAL FIELD

The present invention relates to a benzoselenazolino-vinylspiropyran compound and polymers prepared from the compound.

PRIOR ART

Spiropyran derivatives are best known as typical organic compounds reversibly becoming colored or colorless depending on the light or heat energy condition. Specific examples of these derivatives and physical characteristics thereof are summarized, for example, in G. H. Brown: Photochromism (John Wiley & Sons, Inc., 1971).

For practical use as recording media, however, the so-far known spiropyran derivatives have drawbacks; for instance (1) colored species (or uncolored species), in solutions as well as in macromolecular binders, are lacking in light or heat stability and therefore immediately return to the colorless state (or colored state); (2) in the course of repeated color change (recording and erasing) under the influence of light and heat, the spiropyran derivatives are decomposed or degraded due to side reactions arising from the light irradiation, hence can not have satisfactory repetition cycles; (3) while, for use as photochromic media, the spiropyran derivatives are generally dispersed in an aralkyl group; $R^2$, $R^3$, $R^4$ and $R^5$ are the same or different and each represents a hydrogen atom, an alkyl group having 1 to 6 carbon atoms, an aryl group, an aralkyl group, an alkoxy group having 1 to 5 carbon atoms, a halogen atom, a cyano group, a trichloromethyl group, a trifluoromethyl group or a nitro group; $R^6$ and $R^7$ are the same or different and each represents a hydrogen atom, an alkyl group having 1 to 6 carbon atoms, an aryl group, an aralkyl group, a halogen atom, a cyano group or a nitro group; and X is an oxygen atom or a sulfur atom.

The compound represented by the formula (Ia) of the present invention is a novel compound which has never been heretofore disclosed in the literature and which can be expected to be utilizable in such fields as high-density photo-recording materials, optical filters, image-forming materials, photosensitive materials, nonlinear optical devices, and conversion of light energy to mechanical energy. For example, a polymer which is obtained by dissolving the compound in an appropriate macromolecular compound or copolymerizing the compound with an optional polymerizable compound is uniformly applied to a substrate such as a glass material, whereby optical disk and like high-density recording media can be produced by a conventional procedure.

A macromolecular spiropyran compound which has a desired structure and a desired spiropyran group content can be formed by homopolymerizing the compound represented by the formula (Ia) or by copolymerizing this compound with an appropriate polymerizable compound.

In view of the above, the present invention also provides a polymer of a benzoselenazolino-vinylspiropyran compound which is characterized by comprising (a) 0.001 to 100 mole % of the structural unit represented by the formula

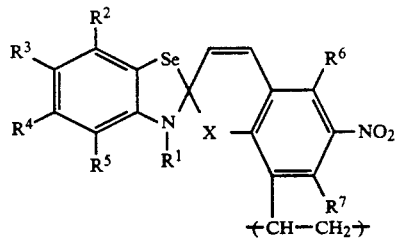

wherein $R^1$ is an alkyl group having 1 to 20 carbon atoms or an aralkyl group; $R^2$, $R^3$, $R^4$ and $R^5$ are the same or different and each represents a hydrogen atom, an alkyl group having 1 to 6 carbon atoms, an aryl group, an aralkyl group, an alkoxy group having 1 to 5 carbon atoms, a halogen atom, a cyano group, a trichloromethyl group, a trifluoromethyl group or a nitro group; $R^6$ and $R^7$ are the same or different and each represents a hydrogen atom, an alkyl group having 1 to 6 carbon atoms, an aryl group, an aralkyl group, a halogen atom, a cyano group or a nitro group; and X is an oxygen atom or a sulfur atom; and (b) 0 to 99.999 mole % of the structural unit represented by the formula

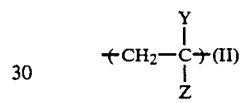

wherein Y is a hydrogen atom or a methyl group; and Z is a carboxyl group, an alkoxycarbonyl group, a cyano group, a carbamoyl group, an N,N-dimethylcarbamoyl group, an acetoxy group, a phenyl group or a methylphenyl group.

The compound of the formula (Ia) of the present invention is designed for obviating the aforementioned drawbacks of the prior art spiropyran derivatives. Stated more specifically, the compound of the formula (Ia) of the invention can be polymerized because the compound has a polymerizable vinyl group, whereby the compound is expected to have, for example, the following advantages in items (1) and (2):

(1) The stability of the compound is improved and there arises substantially no problem of exudation of spiropyran unit from the macromolecular substance; and (2) Films and like media which exhibit photochromism can be formed from the macromolecular substance alone. Further, the compounds of the present invention are chemically bonded to one another through polymer chains, whereby the structure and/or such performance characteristic as polarity, viscosity or solubility can be controlled photoreversibly.

The compounds of the formula (Ia) of the invention are characterized in that the compounds are benzoselenazolinospirobenzopyran compounds or benzoselenazolino-spirobenzothiopyran compounds and that the compounds each have a polymerizable vinyl group in the 8' position of the spirobenzopyran skeleton or spirobenzothiopyran skeleton.

Spiropyran compounds each having a polymerizable substituent at the side chain and the polymers thereof are disclosed, for example, in Nippon Kagaku Kaishi, 1323 (1972), J. Polym. Sci. Polym. Chem. Ed., 12, 2511 (1974), and Japanese Unexamined Patent Publications Nos. 88895/1978, 227972/1984 and 76490/1986. However, these compounds and the polymers are all indolino- or benzothiazolino-spiropyran compounds and the polymers thereof, and are different in chemical structure from the compounds of the formula (Ia) of the invention and the polymers obtained therefrom.

The compounds of the formula (Ia) of the invention are normally (at room temperature) colored, become colorless upon visible light irradiation, and return to the original colored species upon ultraviolet irradiation or heating, thus exhibiting the so-called "negative" photochromism. Further, the benzoselenazolino-spiropyran compound having a vinyl group in the 8' position according to the invention is markedly large in molecular absorption coefficient (a value of $\epsilon$) as compared with the compounds of the following formula (A) each of which is unsubstituted in 8' position, and therefore has sufficient strength of color even at a low concentration thereof.

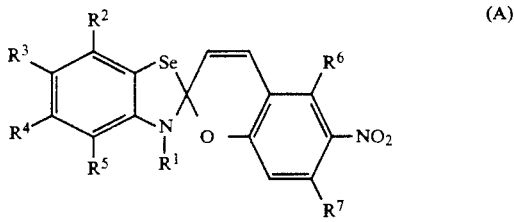
(A)

In the formula, $R^1$, $R^2$, $R^3$, $R^4$, $R^5$, $R^6$ and $R^7$ are as defined above.

The compounds of the formula (Ia) of the invention are very high in durability in the case of repeated color change under the influence of light or heat and light. Furthermore, using the compounds of the invention, the fixation of the uncolored state (unstable system) or the shift from the uncolored state to the colored state can be controlled by adjustment of temperature.

In the benzoselenazolino-vinylspiropyran compounds of the formula (Ia) according to the invention, the aralkyl group is, for example, a phenyl-$C_1$-$C_6$ alkyl group which may optionally have, on its benzene ring, one to five, preferably one, two or three, substituents selected from the group consisting of $C_1$-$C_6$ alkyl group, $C_1$-$C_6$ alkoxy group, halogen atom, cyano group, trichloromethyl group, trifluoromethyl group and nitro group. Examples of the aryl group are a phenyl group and a naphthyl group which may have one to five, preferably one, two or three, substituents selected from the group consisting of $C_1$-$C_6$ alkyl group, $C_1$-$C_6$ alkoxy group, halogen atom, cyano group, trichloromethyl group, trifluoromethyl group and nitro group. Examples of the halogen atom are a fluorine atom, a chlorine atom, a bromine atom, an iodine atom, etc.

Among the compounds of the formula (Ia), preferred are those wherein $R^1$ is an alkyl group having 1 to 20 carbon atoms, $R^2$, $R^3$, $R^4$ and $R^5$ are the same or different and each represents a hydrogen atom, a methyl group, an ethyl group, a phenyl group, a methoxyphenyl group, a methoxy group, an ethoxy group, a fluorine atom, a chlorine atom, a bromine atom, a cyano group or a nitro group, $R^6$ and $R^7$ are the same or different and each represents a hydrogen atom, a methyl group, an ethyl group, a phenyl group or a naphthyl group, and X is an oxygen atom. More preferably compounds are those wherein $R^1$ is an alkyl group having 1 to 18 carbon atoms, each of $R^2$, $R^5$, $R^6$ and $R^7$ is a hydrogen atom, each of $R^3$ and $R^4$ is a hydrogen atom, an alkyl group having 1 to 6 carbon atoms or an alkoxy group having 1 to 5 carbon atoms, and X is an oxygen atom, especially those wherein $R^1$ is a methyl group or an octadecyl group, $R^2$, $R^3$, $R^5$, $R^6$ and $R^7$ are hydrogen atoms, $R^4$ is a hydrogen atom, a methyl group or a methoxy group, and X is an oxygen atom.

As shown in the following reaction scheme, the compound of the formula (Ia) according to the invention can be readily prepared by condensing a quaternary benzoselenazolenium salt derivative represented by the formula (III) with a 5-nitro-3-vinylbenzaldehyde derivative represented by the formula (IV) in the presence of an amine catalyst.

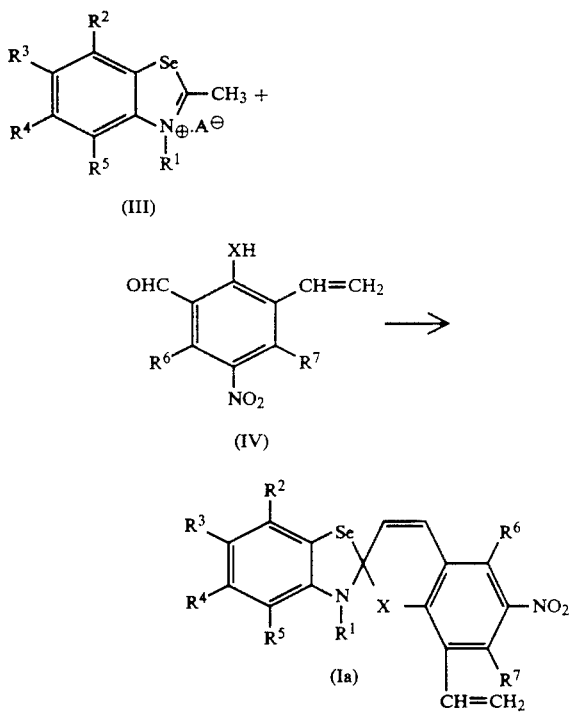

In the formulas, $R^1$, $R^2$, $R^3$, $R^4$, $R^5$, $R^6$, $R^7$ and X are as defined above, A is a chlorine, bromine, iodine or like halogen atom or $R^8SO_3$ group, etc. $R^8$ in the group $R^8SO_3$ is a methyl group, an ethyl group or like lower alkyl group, or a phenyl group which may optionally have fluorine, chlorine, bromine, iodine or like halogen atom or $C_1$-$C_4$ alkyl group as the substituent.

The quaternary benzoselenazolenium salt derivative of the formula (III) which is used as a starting material can be prepared by reacting the corresponding 2-methylbenzoselenazole derivative with at least one mole, preferably 1.05 to 1.5 moles, per mole of the 2-methylbenzoselenazole derivative, of the compound represented by the formula $R^1A$ (wherein $R^1$ and A are as defined above) in a solvent such as chloroform in a sealed tube at a temperature of about 50° to about 150° C. for about 10 to about 48 hours. The 2-methylbenzoselenazole derivative is a known compound set forth in, for example, Ber. 46, 94 (1913), J. Amer. Chem. Soc., 68 1536 (1946) or British patent No. 1411957 (1975), or can be prepared by any one of the processes disclosed in these publications.

On the other hand, the 5-nitro-3-vinylbenzaldehyde derivative of the formula (IV) can be prepared by, for example, the process described in Japanese Unexamined Patent Publication No. 76490/1986. Stated more specifically, first, a salicylaldehyde derivative represented by the formula (V)

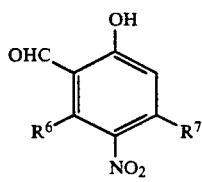

wherein $R^6$ and $R^7$ are as defined above, (this derivative is a known compound disclosed in Beil. 8, 56, or can be prepared by a process set forth in this publication) is reacted with about 2 to about 20 moles, per mole of the derivative (V), of chloromethyl methyl ether in the presence of about 0.5 to about 4 moles, per mole of the derivative (V), of aluminum chloride or like catalyst at about 0° to about 60° C. for 3 to 24 hours, giving a 3-chloromethyl-5-nitrosalicylaldehyde derivative represented by the formula (VI)

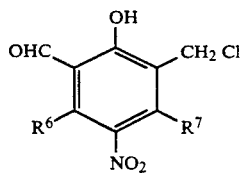

wherein $R^6$ and $R^7$ are as defined above. Subsequently, the compound of the formula (VI) is reacted with about 0.9 to about 1.1 moles, per mole of the compound of the formula (VI), of triphenylphosphine in a solvent such as benzene, toluene or the like at room temperature to around the boiling point of the solvent used for about 2 to about 24 hours, giving a 3-formyl-2-hydroxy-5-nitrobenzyltriphenylphosphonium chloride derivative represented by the formula (VII)

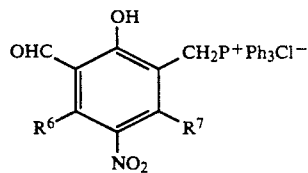

wherein $R^6$ and $R^7$ are as defined above. Further, the compound of the formula (VII) is reacted with about 10 to about 150 moles, per mole of the compound (VII), of paraformaldehyde in a solvent such as dimethylsulfoxide in the presence of an alkaline metal hydroxide or like base at about 0° to about 80° C. for about 1 to about 20 hours, giving a 5-nitro-3-vinylsalicylaldehyde derivative represented by the formula (VIII)

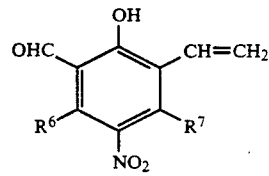

wherein $R^6$ and $R^7$ are as defined above, namely the compound of the formula (IV) wherein X=O.

On the other hand, the compound of the formula (IV) wherein X=S is obtained as follows. That is, the compound of the formula (VIII) obtained above is reacted with N,N-dimethylthiocarbamoyl chloride by, for example, the same procedure as disclosed in Japanese Unexamined Patent Publication No. 54388/1985, giving a 2-O-(N,N-dimethylthiocarbamoyl)benzaldehyde derivative represented by the formula (IX)

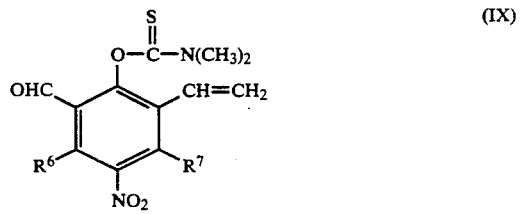

wherein $R^6$ and $R^7$ are as defined above. Thereafter, the compound thus obtained is heated in a solvent such as methanol, ethanol, isopropanol, dimethylformamide, dimethylsulfoxide at about 50° to about 100° C. for about 1 to about 24 hours for rearrangement, giving a 2-S-(N,N-dimethylthiocarbamoyl)benzaldehyde derivative represented by the formula (X)

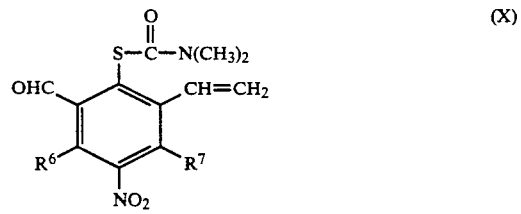

wherein $R^6$ and $R^7$ are as defined above, and the compound thus obtained is subjected to alkali hydrolysis in a solvent such as methanol, ethanol or isopropanol at about 0° to about 50° C. for about 1 to about 120 minutes.

The examples of the preparation of the compound of the formula (III) and the compound of the formula (IV) as the starting materials will be described hereinafter in more detail in Reference Examples 1 to 9.

The aforementioned reaction between the quaternary benzoselenazolenium salt derivative of the formula (III) and the 5-nitro-3-vinylsalicylaldehyde derivative or 5-nitro-3-vinylthiosalicylaldehyde derivative of the formula (IV) can be conducted by dissolving both the reactants in an appropriate solvent, adding an amine to the solution and heating the resulting mixture at a temperature between room temperature and the boiling point of the solvent for about 1 to about 24 hours. A suitable amount of the compound of the formula (III) is about 0.9 to about 1.1 moles per mole of the compound of the formula (IV). The solvent mentioned above may be any of those solvents which can dissolve both of the compounds of the formulas (III) and (IV), for example methanol, acetone, methyl ethyl ketone, ethyl acetate, butyl acetate, dichloromethane, dimethylformamide, etc. Examples of useful amine are piperidine, piperazine, morphorine, triethylamine, pyridine, lutidine, 1,4-diazabicyclo[2,2,2]o-ctane, 1,5-diazabicyclo[4,3,0]nonene, 1,8-diazabicyclo[5,4,0]undecene, etc. A suitable amount of the amine is about 1 to about 10 moles per mole of the compound of the formula (III).

The thus obtained compound of the formula (Ia) according to the invention can be readily isolated from the reaction mixture and purified by conventional separation and purification procedures.

The spiropyran compound of the formula (Ia) of the invention exhibits "negative" photochromism and therefore can be per se utilized for recording materials, photosensitive materials, optical filters, ornamental materials and the like by the same method as disclosed in the foregoing Japanese Unexamined Patent Publications Nos. 88895/1978, 227972/1984, 76490/1986, etc.

As stated hereinbefore, the compound of the formula (Ia) of the invention can be polymerized by itself or copolymerized with another polymerizable compound to produce macromolecular spiropyran compounds which can be applied to use as optical devices or photomechanical devices.

The polymer thus obtained comprises 0.001 to 100 mole of a structural unit of the formula (I)

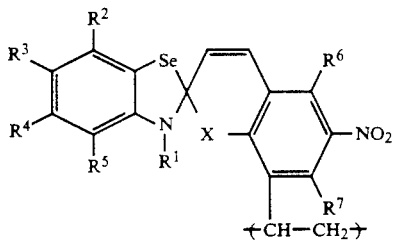

wherein $R^1$, $R^2 R^3$, $R^4$, $R^5$, $R^6$, $R^7$ and X are as defined above, and 0 to 99.999 mole % of a structural unit of the formula

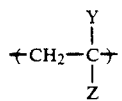

wherein Y and Z are as defined above.

The polymer of the benzoselenazolino-vinylspiropyran compound of the invention is a compound which exhibits photochromism. In the compound of the invention, a spiropyran skeleton has been introduced into a polymer chain through chemical bonding. As a result, (1) the stability of the compound is improved and, at the same time, the above-mentioned prior art problem of exudation or deposition from macromolecular substances is solved; and (2) the compounds of the invention can, by themselves, be molded into films and other media which exhibit photochromism and, as photoresponsive macromolecular compounds, they make it possible to photoreversibly bring out the structure change and/or such performance characteristic as polarity, viscosity or solubility therefrom.

Accordingly, the macromolecular compounds of the invention are compounds which can be utilized in such fields as high-density photo-recording materials, optical filters, image-forming materials, photosensitive materials, nonlinear optical devices, conversion of light energy to mechanical energy and ornamental materials in the same manner as disclosed in the foregoing Japanese Unexamined Patent Publications Nos. 88895/1978, 227972/1984 and 76490/1986. For example, the macromolecular compound of the invention is uniformly applied to a glass or like substrate, whereby high-density recording media such as optical disk can be produced by a conventional method.

In particular, the above macromolecular compounds of the invention are normally (at room temperature) colored, become colorless upon visible light irradiation, and return to the original colored species upon ultraviolet light irradiation or heating or standing in the dark, thus exhibiting the so-called "negative" photochromism.

Further, the colorless species (unstable system) of the above macromolecular benzoselenazolino-vinylspiropyran compound of the invention have much improved stability and much prolonged life as compared with the monomer of the formula (Ia).

In the structural unit of the formula (II), the alkoxy moiety of the alkoxycarbonyl group represented by Z is, for example, of about 1 to about 8 carbon atoms.

Of the structural units of the formula (I), preferred are those corresponding to those preferred among the compounds of the formula (Ia).

Preferred as the structural unit of the formula (II) is the one in which Y is a hydrogen atom or a methyl group and Z is a lower alkoxycarbonyl group, a cyano group or a phenyl group.

The polymer of the benzoselenazolino-vinylspiropyran compound according to the invention has a number average molecular weight of about $1 \times 10^3$ to about $1 \times 10^6$, preferably about $5 \times 10^3$ to about $3 \times 10^5$, as determined by gel permeation chromatography (GPC) (solvent=tetrahydrofuran, temperature=40° C., based on the standard polystyrene) and a weight average molecular weight of about $1 \times 10^3$ to about $2 \times 10^6$, preferably about $5 \times 10^3$ to about $5 \times 10^5$, as determined by the same GPC as mentioned above.

The polymer of the invention may be either homopolymers consisting of the structural unit of the formula (I) alone or copolymers comprising the structural unit of the formula (I) and the structural unit of the formula (II). In such copolymers, the spiropyran structural unit of the formula (I) should be present in said copolymers in an amount of at least 0.001 mole %, especially about 0.001 to about 50 mole preferably about 0.01 to about 25 mole %, more preferably about 0.1 to about 10 mole %, with the balance accounting for the structural unit of the formula (II), since the desired photochromism can not be attained when the content of the spiropyran structural unit of the formula (I) is too small.

The compounds of the present invention are prepared by homopolymerization of the benzoselenazolino-vinylspiropyran compound of the formula (Ia) which formula corresponds to the structural unit of the formula (I), or copolymerization of said compound of the formula (Ia) with a polymerizable vinyl monomer represented by the formula (IIa)

wherein Y and Z are as defined above, which formula corresponds to the structural unit of the formula (II).

The vinyl monomer of the above formula (IIa) includes known ones only. Thus, for example, methacrylic acid, acrylic acid, $C_1$–$C_8$ alkyl esters of methacrylic acid or acrylic acid, acrylonitrile, acrylamide, N,N-dimethylacrylamide, vinyl acetate, styrene, α- methylstyrene, vinyltoluene, and the like are suitably used.

The above-mentioned homopolymerization and copolymerization can be carried out in the same manner and under the same conditions as the synthetic reactions for conventional vinyl resins and the like. For example, the monomeric compound of the formula (Ia) is dissolved, either alone or together with the compound of the formula (IIa), in an organic solvent and heating the solution in the presence of a radical polymerization initiator at a temperature of about 50° to about 100° C. with stirring. The reaction time is usually about 1 to about 150 hours. Usable as the organic solvent are those which are inert to the monomer(s) used and the polymer obtained, for example polar organic solvents of the amide type such as N,N-dimethylformamide and the like, ether solvents such as diethyl ether, tetrahydrofuran, dimethoxyethane, diglyme and the like, hydrocarbon solvents such as benzene, toluene, xylene and the like, ester solvents such as ethyl acetate, butyl acetate, methyl propionate and the like, ketone solvents such as acetone, methyl ethyl ketone, methyl isobutyl ketone and the like, etc. The radical initiator may be any of those commonly used and includes, as typical examples, peroxides such as benzoyl peroxide, di-t-butyl peroxide, t-butyl peroxy-2-ethylhexanoate and the like, azo compounds such as azobisisobutyronitrile, azobisdimethylvaleronitrile and the like, Grignard reagents such as phenylmagnesium bromide and the like, etc.

In cases where the compound of the invention is a copolymer comprising the structural unit of the formula (I) and the structural unit of the formula (II), the proportions of both structural units in the copolymer (copolymerization ratio) is determined by such factors as the charge ratio between the benzoselenazolino-vinylspiropyran compound of the formula (Ia) and the vinyl compound of the formula (IIa) and the method of copolymerization. Therefore, if the relevant relationship is determined in advance with such factors as parameters, the copolymer can be readily produced with a desired copolymerization ratio.

The thus-produced macromolecular vinylspirobenzopyran compound of the invention can be isolated by a conventional procedure. For example, the reaction mixture after completion of the polymerization reaction is added dropwise to a poor solvent for the polymer such as methanol, ether or the like to cause precipitation of said compound as a solid. Said solid can be collected by filtration, for instance.

The macromolecular benzoselenazolino-vinylspiropyran compound obtained above and the monomer of the formula (Ia) as the starting material are both stably colored at normal temperatures and become colorless (metastable state) upon visible light irradiation, thus exhibiting the so-called "negative" photochromism. However, the macromolecular benzoselenazolino-vinylspiropyran compound of the invention is characterized in that the colorless species (metastable state) of the compound have much improved stability and much prolonged life as compared with the monomer of the formula (Ia).

EXAMPLES

The present invention will be described below in greater detail with reference to the following examples.

Figure 2:
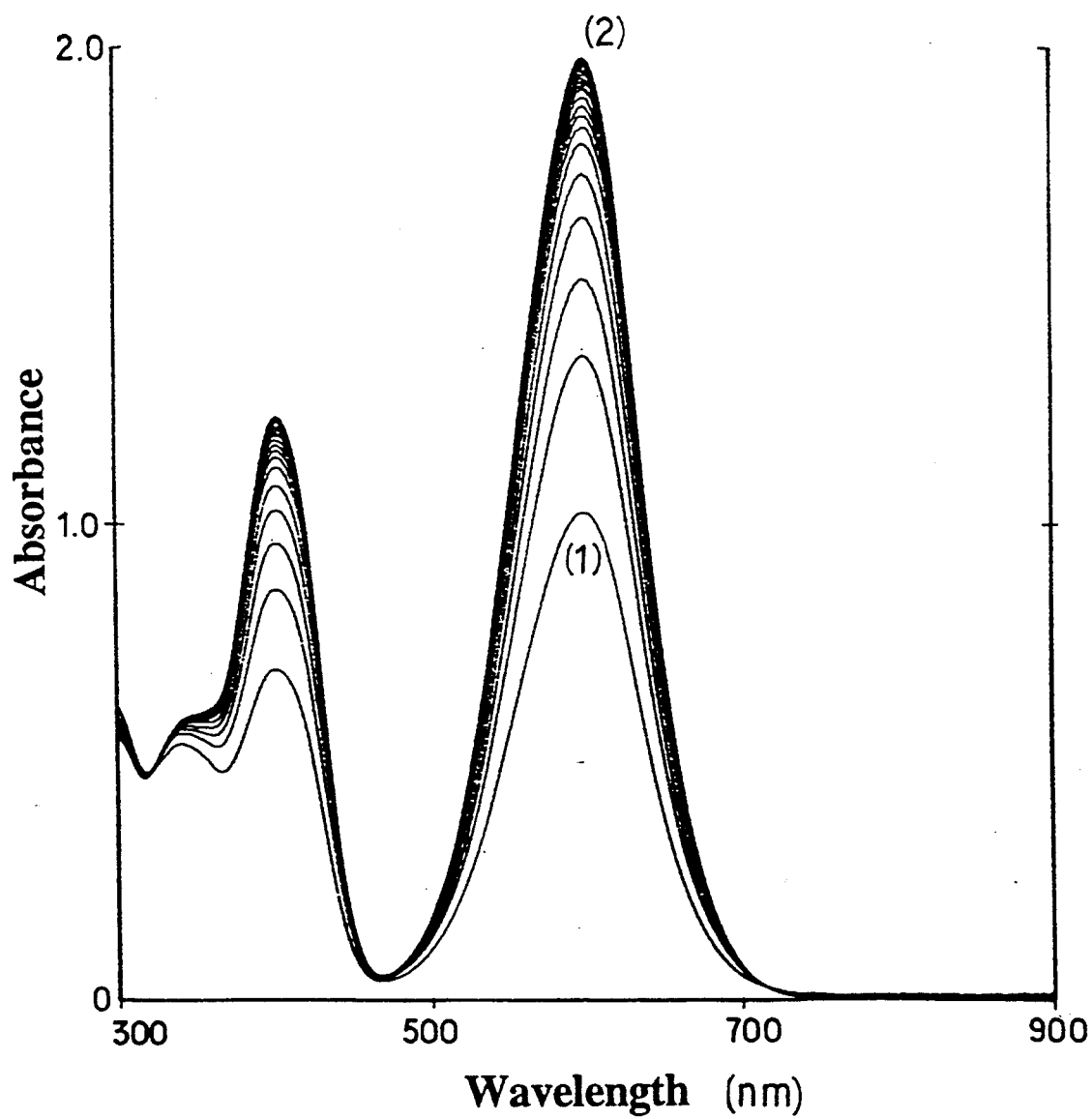

FIGS. 1 and 2 each show visible light absorption spectra measured at 3- or 2-minute intervals after completion of visible light irradiation of each solution of the compound of the invention in chloroform obtained in Examples and 2, respectively until the coloration reaches equilibrium.

Figure 3:
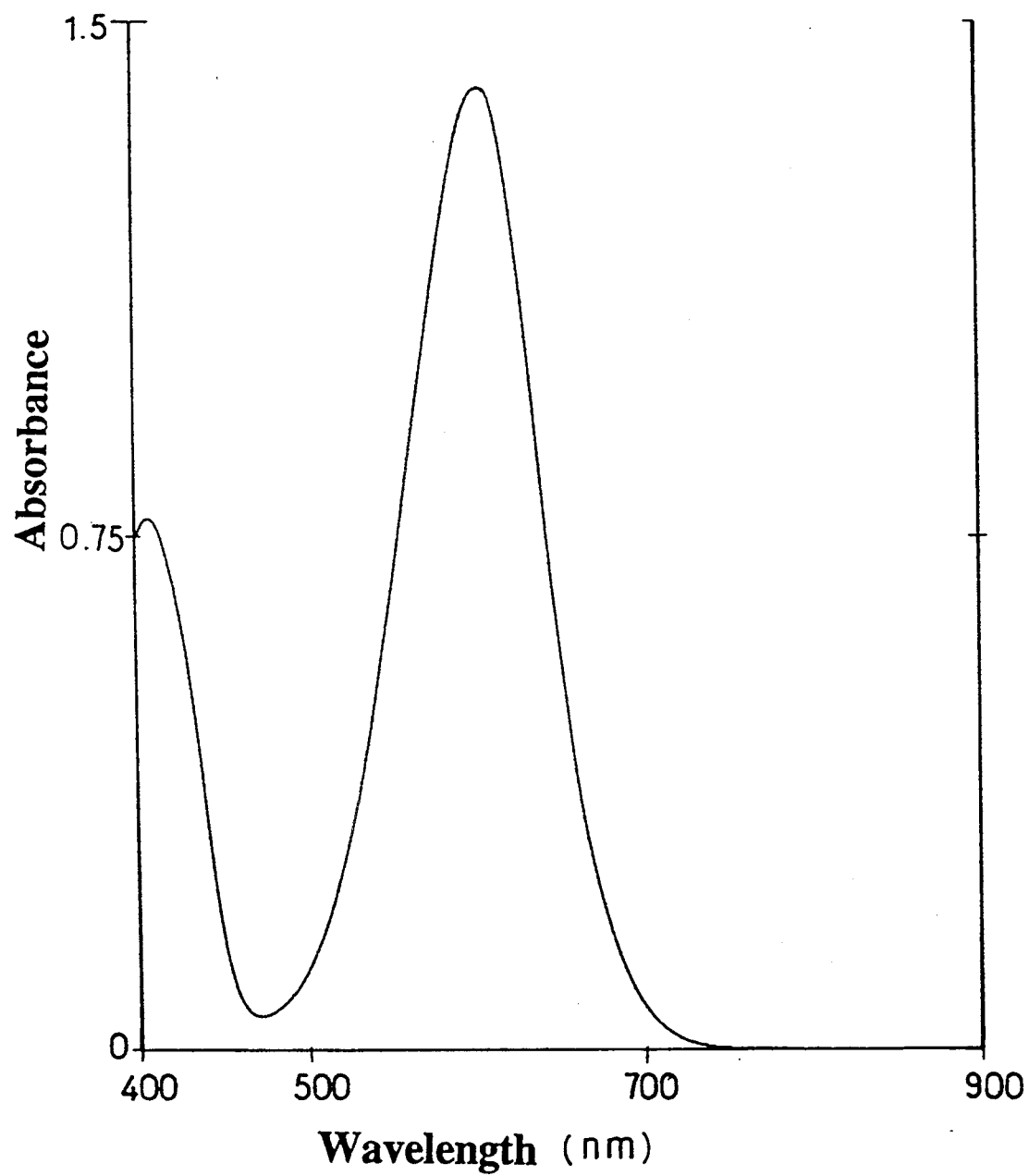

FIG. 3 shows a visible light absorption spectrum measured at the time when the coloration of the compound of the invention obtained in Example 3 reaches equilibrium.

In FIGS. 1 and 2, designated (1) is a spectrum measured by starting the measurement immediately after the solution is made colorless by the visible light irradiation; and designated (2) is a spectrum measured at the time when the coloration reaches equilibrium.

Figure 4:
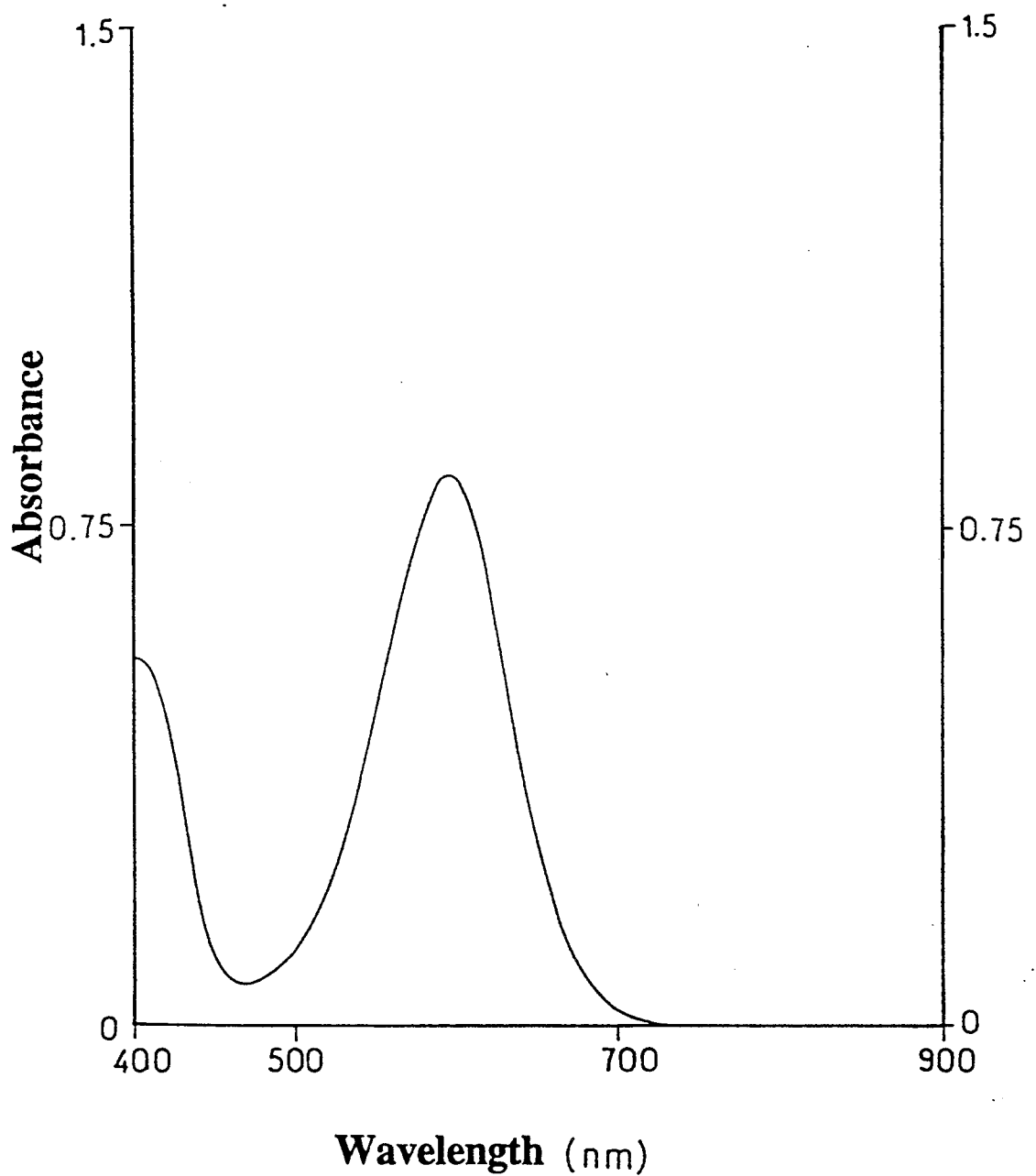

FIG. 4 shows a visible light absorption spectrum measured at the time when the coloration reaches equilibrium after making a solution of the polymer of the invention in chloroform obtained in Example 7 colorless and transparent by visible light irradiation and allowing the solution to return to its colored state by standing the solution at 25° C.

Figure 5:
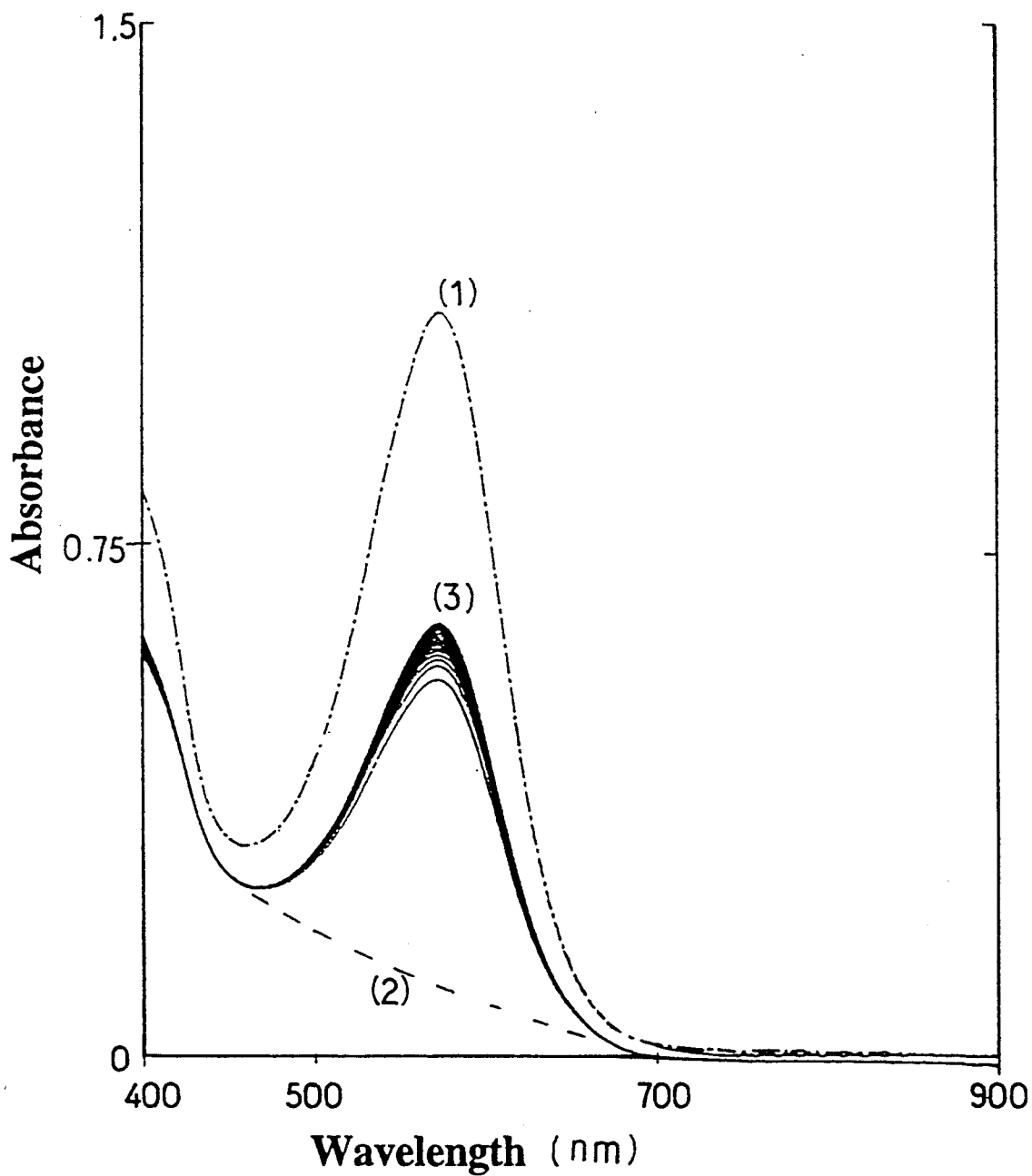

FIG. 5 shows visible light absorption spectra at room temperature of the film of the polymer according to the invention obtained in Example 9. In FIG. 5, designated (1) is the spectrum just after film manufacture; designated (2) is the spectrum immediately after completion of visible light irradiation; and designated (3) is the spectrum at the time when, after gradual coloration following visible light irradiation, no further coloration is eventually observable (fixation of the colorless species has been achieved).

Reference Examples 1 to 9 indicate the examples of the preparation of benzoselenazolino-vinylspiropyran compound (monomer) represented by the foregoing formula (Ia).

REFERENCE EXAMPLE 1

A 43.9 g (0.33 mole) quantity of anhydrous aluminum chloride was added in small portions to a mixture of 12.0 g (71.8 mmoles) of 5-nitrosalicylaldehyde and 100 ml of chloromethyl methyl ether with cooling in an ice bath. The resulting mixture was stirred at room temperature for 10 minutes and refluxed with heating for 22 hours. Thereafter, the reaction mixture was cooled in an ice bath, followed by addition of 200 ml of water with thorough stirring, whereby white crystals were precipitated. The white crystals were collected, dissolved in hot hexane and filtered. The mother liquor was cooled, giving 14.9 g (yield: 72%) of 3-chloromethyl-5-nitrosalicylaldehyde as colorless needle crystals.

$^1$H-NMR (CDCl$_3$); δ ppm 4.72 (s, 2H, —CH$_2$Cl), 8.56 (s, 2H, ArH), 10.00 (s, 1H, CHO), 12.10 (s, 1H, OH)

REFERENCE EXAMPLE 2

A 4.53 g (20.9 mmoles) quantity of 3-chloromethyl-5-nitrosalicylaldehyde and 5.48 g (20.9 mmoles) of triphenylphosphine were dissolved in 30 ml of benzene and the solution obtained was refluxed with heating for 8 hours. After the reaction, the precipitate obtained was isolated by filtration, washed thoroughly with acetone and dried, giving 8.63 g (yield: 86%) of 3-formyl-2-hydroxy-5-nitrobenzyltriphenylphosphonium chloride as a yellow powder.

Melting point: 212°–216° C.
IR:1510, 1430, 1330, 1280 cm$^{-1}$

REFERENCE EXAMPLE 3

A 50.1 g (1.67 moles) quantity of paraformaldehyde was dissolved in 60 ml of water with heating, and a solution of 7.04 g (14.7 mmoles) of 3-formyl-2-hydroxy- 5-nitrobenzyltriphenylphosphonium chloride in 100 ml of dimethylsulfoxide was added thereto, giving a homogeneous solution. Thereafter, a 12N aqueous solution of sodium hydroxide was gradually added to the solution at room temperature and the reaction was effected for 11 hours. A 260 ml quantity of water was added to the reaction mixture and the precipitated crystals of triphenylphosphine oxide were separated by filtration. The filtrate obtained was neutralized with diluted hydrochloric acid, followed by extraction with ether. The liquid extract was concentrated and the residue was recrystallized using chloroform, giving 1.23 g (yield: 3%) of 5-nitro-3-vinylsalicylaldehyde as yellow crystals.

Melting point: 144.5°–145.5° C.

NMR(CDCl$_3$); δ ppm 5.5 (d, 1H, vinyl), 6.0 (d, 1H, vinyl), 7.0 (dd, 1H, vinyl), 8.5 (m, 2H, Ar—H), 10.0 (s, 1H, —CHO), 12.1 (s, 1H, OH)

REFERENCE EXAMPLE 4

Into a sealed tube were placed 3.92 g (20.0 mmoles) of 2-methylbenzoselenazole, 3.87 g (20.8 mmoles) of methyl paratoluenesulfonate and 20 ml of chloroform, giving a homogeneous solution. The solution obtained was heated at 100° C. for 2 days. The reaction mixture was concentrated and the residue was washed with ether, followed by drying under reduced pressure, giving 7.26 g (yield: 95%) of 2,3-dimethylbenzoselenazolium paratoluenesulfonate as a purple powder.

NMR (D$_2$O); δ ppm 2.4 (s, 3H, CH$_3$—Ar), 3.2 (s, 3H,

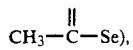

4.2 (s, 3H, CH$_3$N), 7.2-8.2 (m, 8H, Ar—H)

REFERENCE EXAMPLE 5

Into a sealed tube were placed 4.20 g (20.0 mmoles) of 2,5-dimethylbenzoselenazole, 3.90 g (21.0 mmoles) of methyl paratoluenesulfonate and 20 ml of chloroform. A reaction and treatment were conducted by the same procedure as in Reference Example 4, giving 7.62 g (yield: 96%) of 2,3,5-trimethylbenzoselenazolium paratoluenesulfonate as a pink powder.

NMR(D$_2$O); δ ppm 2.2 (s, 3H, CH$_3$—Ar), 2.6 (s, 3H,

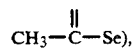

3.2 (s, 3H, CH$_3$—N), 7.1-8.1 (m, 7H, Ar—H)

REFERENCE EXAMPLE 6

Into a sealed tube were placed 2.26 g (10.0 mmoles) of 5-methoxy-2-methylbenzoselenazole, 1.93 g (10.4 mmoles) of methyl paratoluenesulfonate and 10 ml of chloroform. The resulting mixture was treated in the same manner as in Reference Example 4, giving 4.07 g (yield: 99%) of 5-methoxy-2,3-dimethylbenzoselenazolium paratoluenesulfonate as a purple powder.

NMR (D$_2$O); δ ppm 2.4 (s, 3H, CH$_3$—Ar), 3.2 (s, 3H,

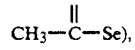

4.0 (s, 3H, CH$_3$O), 4.1 (s, 3H, CH$_3$—N), 7.2-8.1 (m, 7H, Ar—H)

REFERENCE EXAMPLE 7

Into a sealed tube in which air was replaced by nitrogen were placed 1.50 g (7.4 mmoles) of 2-methylbenzoselenazole and 3.34 g (7.5 mmoles) of octadecyl parachlorobenzenesulfonate. The resulting mixture was heated at 130° C. for 5 hours. The reddish purple solid obtained was washed with ether and recrystallized from n-propanol, giving 2.40 g (yield: 50.5%) of 2-methyl-3-octadecylbenzoselenazolium parachlorobenzenesulfonate as a reddish purple powder.

NMR (DMSO-d$_6$); δ ppm 0.8 (t, 3H, CH$_3$—), 1.2 (s, 28H, $+CH_2\overline{)_{14}}$), 1.4 (bs, 2H, —CH$_3$—), 1.8 (bs, 2H, —CH$_3$—), 3.2 (s, 3H,

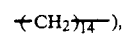

4.6 (t, 2H, —CH$_2$—N), 7.2-8.3 (m, 8H, Ar—H)

REFERENCE EXAMPLE 8

Into a sealed tube in which air was replaced by nitrogen were placed 1.50 g (7.14 mmoles) of 2,5-dimethylbenzoselenazole and 3.50 g (7.85 mmoles) of octadecyl parachlorobenzenesulfonate. The mixture obtained was heated at 130° C. for 3 hours. The resulting red solid was washed with ether and dried under reduced pressure, giving 2.69 g (yield: 57.4%) of 2,5-dimethyl-3-octadecylbenzoselenazolium parachlorobenzenesulfonate as a light brown powder.

NMR (DMSO-d$_6$); δ ppm 0.8 (t, 3H, CH$_3$—), 1.2 (s, 28H, $+CH_2\overline{)_{14}}$), 1.4 (bs, 2H, —CH$_2$—), 1.8 (bs, 2H, —CH$_2$—), 2.5 (s, 3H, CH$_3$—Ar), 3.2 (s, 3H,

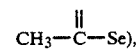

4.6 (t, 2H, —CH$_2$—N), 7.3-8.3 (m, 7H, Ar—H)

REFERENCE EXAMPLE 9

Into a sealed tube in which air was replaced by nitrogen were placed 0.50 g (2.17 mmoles) of 5-methoxy-2-methylbenzoselenazole and 1.06 g (2.39 mmoles) of octadecyl parachlorobenzenesulfonate. The mixture obtained was heated at 130° C. for 4 hours. The resulting reddish purple solid was washed with ether and dried under reduced pressure, giving 0.72 g (yield: 49.3%) of 5-methoxy-2-methyl-3-octadecylbenzoselenazolium parachlorobenzenesulfonate as a reddish purple powder.

NMR (DMSO-d$_6$); δ ppm 8 (t, 3H, CH$_3$—), 1.2 (s, 28H,

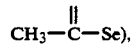

1.4 (bs, 2H, —CH$_2$—), 1.8 (bs, 2H, —CH$_2$—), 3.2 (s, 3H, $$CH_3-\overset{\overset{O}{\|}}{C}-Se),$$

3.9 (s, 3H, CH$_3$O), 4.6 (t, 2H, —CH$_2$—N), 7.3–8.3 (m, 7H, Ar—H)

EXAMPLE 1

Into a reactor in which air was replaced by nitrogen were placed 386 mg (2.00 mmoles) of 5-nitro-3-vinylsalicylaldehyde, 772 mg (2.02 mmoles) of 2,3-dimethylbenzoselenazolium paratoluenesulfonate and 10 ml of methanol, giving a homogeneous solution. To the solution was added a solution of 170 mg (2.00 mmoles) of piperidine in 5 ml of methanol, and the resulting mixture was refluxed with heating for 24 hours. The liquid reaction mixture was cooled to room temperature, and the precipitate obtained was isolated by centrifugation, washed with methanol and dried in a vacuum, giving 603 mg (yield: 78%) of 3-methyl-6'-nitro-8'-vinylspiro[benzoselenazolin-2,2'(2'H)-1'-benzopyran] as a blackish green powder.

IR (KBr) 1510, 1330 cm$^{-1}$ $^1$H-NMR (DMSO-d$_6$); δ ppm 4.14 (s, 3H, CH$_3$—N), 5.19 (dd, 1H, vinyl), 6.01 (dd, 1H, vinyl), 6.95 (dd, 1H, vinyl), 7.61 (t, 1H, 6-H), 7.74 (t, 1H, 5-H), 8.04 (d, 1H, 5' or 7'-H), 8.08 (d, 1H, 7-H), 8.21 (d, 1H, 4'-H), 8.34 (d, 1H, 4-H), 8.52 (d, 1H, 7' or 5'-H), 8.69 (d, 1H, 3'-H)

MS (EI, 70 ev): 385(M$^+$)

The photochromic properties of the compound obtained above in Example 1 were determined. A solution of this compound in chloroform which was obtained by dissolving 26 mg of the compound per liter of chloroform was transparent deep blue at room temperature and had an absorption maximum at 598 nm. When the solution was irradiated with visible rays for 2 minutes with use of a 500-W ultra-high pressure mercury lamp equipped with a cut-off filter allowing passage of visible rays not shorter than 500 nm in wavelength, the initially observed absorption maximum peak disappeared and the solution became colorless and transparent. When maintained at 25° C., this solution already became blue one minute later, and turned deep blue again within a period of one hour. Visible light absorption spectra were measured at 3-minute intervals over a period of about one hour immediately after the visible light irradiation until the colored state reached equilibrium, with the results shown in FIG. 1. The half-life of the uncolored species was not longer than about 30 seconds at 25° C. and the molecular absorption coefficient of the compound was ε=11000 at the absorption maximum wavelength.

On the other hand, a transparent colorless solution obtained by maintaining the above solution at 0° C. and irradiating the solution with the same visible rays as above for one minute was very stable at this temperature. The solution assumed no color 12 hours later and remained colorless. When this colorless solution was irradiated with ultraviolet rays at 0° C. for one minute using a 500-W ultrahigh pressure mercury lamp equipped with a cut-off filter allowing passage of ultraviolet rays having a wavelength of about 350 nm, the solution turned transparent deep blue again. Further, when the solution was subjected to a cycle repeatedly 100 times, one cycle consisting of color fading by means of visible light and coloration by means of ultraviolet light, the absorbance of the solution in the colored state did not decrease at all during the cycles, whereby the cycle could be repeated with reproducibility.

When the above chloroform solution which was transparent deep blue at room temperature was made into a transparent colorless solution by visible light irradiation at 0° C. in the same manner as above and then maintained at 25° C. for 30 minutes, the solution returned to its original transparent deep blue color. This procedure was taken as one cycle. This cycle could be repeated at least 30 times with reproducibility. During the cycles, the absorbance of the solution in the colored state never decreased and the solution was ready for being subjected to the cycle repeatedly many more times.

EXAMPLE 2

Into a reactor in which air was replaced by nitrogen were placed 579 mg (3.0 mmoles) of 5-nitro-3-vinylsalicylaldehyde, 1.20 g (3.03 mmoles) of 2,3,5-trimethylbenzoselenazolium paratoluenesulfonate and 20 ml of methanol, giving a homogeneous solution. To the solution was added a solution of 280 mg (3.03 mmoles) of piperidine in 5 ml of methanol, and the mixture obtained was refluxed with heating for 24 hours. The resulting reaction mixture was treated in the same manner as in Example 1, giving 962 mg (yield: 80%) of 3,5-dimethyl-6'-nitro-8'-vinylspiro[benzoselenazolin- 2,2'(2'H)-1'-benzopyran] as a blackish green powder.

IR (KBr) 1510, 1330 cm$^{-1}$ $^1$-NMR (DMSO-d$_6$); δ ppm 2.49 (s, 3H, CH$_3$—Ar), 4.09 (s, 3H, CH$_3$—N), 5.16 (dd, 1H, vinyl), 5.97 (dd, 1H, vinyl), 6.91 (dd, 1H, vinyl), 7.41 (d, 1H, 6-H), 7.91 (s, 1H, 4-H), 8.00 (d, 1H, 5' or 7'-H), 8.15 (d, 1H, 3' or 4'-H), 8.16 (d, 1H, 7-H), 8.47 (d, 1H, 7' or 5'-H), 8.65 (d, 1H, 4' or 3'-H)

MS (EI, 70 ev): 399(M$^+$)

The photochromic properties of the compound obtained above in Example 2 were determined. A solution of the compound in chloroform prepared by dissolving 27.6 mg of the compound per liter of chloroform was transparent deep blue at room temperature and had an absorption maximum at 601 nm. When this solution was irradiated with visible rays in the same manner a in Example 1, the initially observed absorption maximum peak disappeared and the solution became colorless and transparent. This solution gradually became colored at 26° C., and turned deep blue again when maintained at the same temperature for about 1 hour. Visible light absorption spectra were determined at 2-minute intervals over a period of about 1 hour immediately after completion of the visible light irradiation until the colored state reached equilibrium with the results shown in FIG. 2.

The results showed that the compound of the present invention exhibited "negative" photochromism. The half-life of the uncolored species was 1.7 minutes at 26° C., and λmax=601 nm and the molecular absorption coefficient at this wavelength was ε=29000.

On the other hand, the above solution was maintained at 0° C. and irradiated with the same visible rays as used in Example 1 for 1 minute, giving a transparent colorless solution. This transparent colorless solution was very stable at this temperature, assumed no color 12 hours later and remained colorless. When the colorless solution was irradiated with ultraviolet rays at 0° C. for 1 minute with use of a 500-W ultra-high pressure mercury lamp equipped with a cut-off filter allowing passage of ultraviolet rays having a wavelength of about 350 nm, the solution turned transparent deep blue again. Further, the solution was subjected to a cycle repeatedly 100 times, one cycle consisting of color fading by means of visible light and coloration by means of ultraviolet light. Consequently, the absorbance of the solution in the colored state was not decreased during the 100 cycles, and the cycle could be repeated with reproducibility.

The foregoing chloroform solution which was transparent deep blue at room temperature was irradiated with visible rays at 0° C. in the same manner as above, giving a transparent, colorless solution. When this solution was maintained at 25° C. for 30 minutes, the solution turned transparent deep blue again. This procedure was taken as one cycle. This cycle could be repeated at least 30 times with reproducibility. During the cycles, no reduction of the absorbance of the solution in the colored state was found and the solution was ready for being subjected to the cycle repeatedly many more times.

EXAMPLE 3

Into a reactor in which air was replaced by nitrogen were placed 386 mg (2.00 mmoles) of 5-nitro-3-vinylsalicylaldehyde, 832 mg (2.02 mmoles) of 5-methoxy-2,3-dimethylbenzoselenazolium paratoluenesulfonate and 10 ml of methanol, giving a homogeneous solution. To the solution was added a solution of 300 mg (2.8 mmoles) of piperidine in 5 ml of methanol, and the resulting mixture was refluxed with heating for 21 hours. The obtained reaction mixture was treated in the same manner as in Example 1, giving 582 mg (yield: 70%) of 5-methoxy-3-methyl-6'-nitro-8'-vinylspiro[benzoselenazolin-2,2'(2'H)-1'-benzopyran] as a blackish green powder.

IR (KBr) 1510, 1330 cm$^{-1}$ $^1$H-NMR (DMSO-d$_6$); δ ppm 3.91 (s, 3H, CH$_3$O), 4.09 (s, 3H, CH$_3$—N), 5.15 (dd, 1H, vinyl), 5.96 (dd, 1H, vinyl), 6.91 (dd, 1H, vinyl), 7.20 (dd, 1H, 6-H), 7.55 (d, 1H, 4-H), 7.98 (d, 1H, 7'-H), 8.11 (d, 1H, 3, or 4'-H), 8.15 (d, 1H, 7-H), 8.44 (d, 1H, 7' or 5'-H), 8.64 (d, 1H, 4' or 3'-H)

The photochromic properties of the compound obtained above in Example 3 were determined. A solution of the compound in chloroform which was prepared by dissolving 21.2 mg of the compound per liter of chloroform was transparent deep blue at room temperature and had an absorption maximum at 606 nm. When the solution was irradiated with visible rays in the same manner as in Example 1, the initially observed absorption maximum peak disappeared and the solution became colorless and transparent. This solution gradually assumed a color at 25° C. and turned deep blue again when maintained at the same temperature for about 1 hour. FIG. 3 shows the visible light absorption spectrum measured at the time when the colored state of the solution reached equilibrium.

This result shows that the compound of the present invention exhibited "negative" photochromism and that the half-life of the uncolored species was 2.9 minutes at 25° C. Further, λmax = 606 nm and the molecular absorption coefficient was ε=28000 at this wavelength.

On the other hand, the above solution was maintained at 0° C. and irradiated with the same visible rays as used in Example for minute, giving a transparent, colorless solution. This solution was very stable at this temperature, assumed no color 12 hours later and remained colorless. When the colorless solution was irradiated with ultraviolet rays at 0° C. for 1minute with use of a 500-W ultra-high pressure mercury lamp equipped with a cut-off filter allowing passage of ultraviolet rays having a wavelength of about 350 nm, the solution turned transparent deep blue again. Further, the solution was subjected to a cycle repeatedly 100 times, one cycle consisting of color fading by means of visible light and coloration by means of ultraviolet light. During the 100 cycles, the absorbance of the solution in the colored state never decreased, and the solution could be subjected to the cycle repeatedly with reproducibility.

The aforementioned chloroform solution which was transparent deep blue at room temperature was irradiated with visible rays in the same manner as above at 0° C., giving a transparent, colorless solution. When this solution was maintained at 25° C. for 30 minutes, the solution returned to its original transparent deep blue color. This procedure was taken as one cycle. This cycle could be repeated at least 30 times with reproducibility. During the cycles, the absorbance of the solution in the colored state was never reduced, and the solution was ready for being subjected to the cycle repeatedly many more times.

EXAMPLE 4

Into a reactor in which air was replaced by nitrogen were placed 0.45 g (2.33 mmoles) of 5-nitro-3-vinylsalicylaldehyde, I.50 g (2.33 mmoles) of 2-methyl-3-octadecylbenzoselenazolium parachlorobenzenesulfonate and 45 ml of methanol, giving a homogeneous solution. To the solution was added a solution of 0.21 g (2.44 mmoles) of piperidine in 7 ml of methanol, and the resulting mixture was refluxed with heating for 6 hours. The reaction mixture obtained was cooled to room temperature and the resulting precipitate was separated by filtration, washed with methanol and dried in a vacuum, giving 1.28 g (yield: 88 4%) of 6'-nitro-3-octadecyl-8'-vinylspiro[benzoselenazolin-2,2'(2'H)-1'-benzopyran] as a dark brown powder.

IR (KBr) 1505, 1300 cm$^{-1}$ $^1$-NMR (CDCl$_3$); δ ppm 0.87 (t, 3H, CH$_3$), 1.24 (s, 28H,

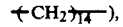

1.50 (m, 2H, —CH$_2$—), 1.90 (m, 2H, —CH$_2$—), 4.43 (t, 2H, —CH$_2$—N), 5.26 (dd, 1H, vinyl), 5.85 (dd, 1H, vinyl), 7.04 (dd, 1H, vinyl), 7.45–7.67 (m, 4H, 4-H, 5-H, 6-H, 7-H, 4'-H), 7.84 (d, 1H, 4-H), 8.01 (d, 1H, 5'-H or 7'-H), 8.05 (d, 1H, 7'-H or 5'-H), 8.81 (bs, 1H, 3'-H)

MS (FD, 18 mA) M/Z=624

The photochromic properties of the compound obtained above in Example 4 were determined. A solution of the compound in chloroform which was prepared by dissolving 30 mg of the compound per liter of chloroform was transparent deep blue at room temperature, and had an absorption maximum at 598 nm. When this solution was irradiated with visible rays for 1 minute using a 500-W ultra-high pressure mercury lamp equipped with a cut-off filter allowing passage of visible rays not shorter than 500 nm in wavelength, the initially observed absorption maximum peak disappeared and the solution became colorless and transparent. When maintained at 23° C., this solution assumed a blue color one minute later and turned deep blue again within a period of 1 hour. The molecular absorption coefficient of the compound was $\epsilon=29900$ at a maximum wavelength.

On the other hand, the foregoing solution was maintained at 0° C. and irradiated with the same visible rays as above for 1 minute, giving a transparent, colorless solution. This solution was very stable at this temperature. When the colorless solution was irradiated with ultraviolet rays at 0° C. for 1minute with use of a 500-W ultra-high pressure mercury lamp equipped with a cut-off filter allowing passage of ultraviolet rays having a wavelength of about 350 nm, the solution turned deep blue again. Further, the solution was subjected to a cycle repeatedly 100 times, one cycle consisting of color fading by means of visible light and coloration by means of ultraviolet light. During the 100 cycles, the absorbance of the solution in the colored state was never reduced, and the solution could be subjected to the cycle repeatedly with reproducibility.

Furthermore, the chloroform solution which was transparent deep blue at room temperature was irradiated with visible rays at 0° C. in the same manner as above, giving a transparent, colorless solution. When maintained at 25° C. for 30 minutes, the solution turned to its original transparent deep blue color. In the case where this cycle was taken as one cycle, the solution could be subjected to at least 30 cycles with reproducibility. During the cycles, the absorbance of the solution in the colored state was never reduced, and the solution was ready for being subjected to the cycle repeatedly many more times.

EXAMPLE 5

Into a reactor in which air was replaced by nitrogen were placed 1.70 g (2.60 mmoles) of 5-nitro-3-vinylsalicylaldehyde, 0.50 g (2 60 mmoles) of 2,5-dimethyl-3-octadecylbenzoselenazolium parachlorobenzenesulfonate and 50 ml of methanol, giving a homogeneous solution. To the solution obtained was added a solution of 0.24 g (2.80 mmoles) of piperidine in 10 ml of methanol, and the resulting mixture was refluxed with heating for 3 hours. The reaction mixture thus obtained was cooled to room temperature, and the precipitate obtained was separated by filtration, washed with methanol and dried in a vacuum, giving 1.04 g (yield: 62.6%) of 6'-nitro-5-methyl-3-octadecyl-8'-vinylspiro[benzoselenazolin-2,2'(2'H )-1'-benzopyran] as a dark brown powder.

IR (KBr) 1524, 1306 cm$^{-1}$ $^1$H-NMR (CDCl$_3$); δ ppm 0.87 (t, 3H, CH$_3$—), 1.24 (s, 28H,

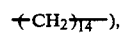

1.46 (m, 2H, —CH$_2$—), 1.89 (m, 2H, —CH$_2$—), 2.53 (s, 3H, CH$_3$—Ar), 4.38 (t, 2H, —CH$_2$—N), 5.27 (dd, 1H, vinyl), 5 86 (dd, 1H, vinyl), 7.04 (dd, 1H, vinyl), 7.21 (s, 1H, 4-H), 7.27 (d, 1H, 6-H), 7.55 (d, 1H, 4'-H), 7.67 (d, 1H, 7-H), 7.94 (d, 1H, 5' or 7'-H), 7.98 (d, 1H, 7' or 5'-H), 8.78 (d, 1H, 3'-H)

The photochromic properties of the compound obtained above in Example 5 were determined. A solution of the compound in chloroform which was prepared by dissolving 30 mg of the compound per liter of chloroform was transparent deep blue at room temperature, and had an absorption maximum at 595 nm. When this solution was irradiated with visible rays for 1 minute with use of a 500-W ultra-high pressure mercury lamp equipped with a cut-off filter allowing passage of visible rays not shorter than 500 nm in wavelength, the initially observed absorption maximum peak disappeared and the solution became colorless and transparent. When maintained at 23° C., this solution assumed a blue color one minute later and turned deep blue again within a period of hour. The molecular absorption coefficient of the compound was $\epsilon=35600$ at a maximum wavelength.

The foregoing solution was maintained at 0° C. and irradiated with the same visible rays as above for 1 minute, giving a transparent, colorless solution. This solution was very stable at this temperature. When the solution was irradiated with ultraviolet rays at 0° C. for 1 minute using a 500-W ultra-high pressure mercury lamp equipped with a cut-off filter allowing passage of ultraviolet rays having a wavelength of about 350 nm, the solution turned deep blue again. The solution was further subjected to a cycle repeatedly 100 times, one cycle consisting of color fading by means of visible light and coloration by means of ultraviolet light. During the 100 cycles, the absorbance of the solution in the colored state was never reduced, and the solution could be subjected to the cycle repeatedly with reproducibility.

The chloroform solution which was transparent deep blue at room temperature was irradiated with visible rays at 0° C. in the same manner as above, giving a transparent, colorless solution. When maintained at 25° C. for 30 minutes, the solution returned to its original transparent deep blue color. In the case where this procedure was taken as one cycle, the solution could be subjected to the cycle repeatedly at least 30 times with reproducibility. During the cycles, the absorbance of the solution in the colored state was never reduced, and the solution was ready for being subjected to the cycle repeatedly many more times.

EXAMPLE 6

Into a reactor in which air was replaced by nitrogen were placed 112 mg (0.58 mmole) of 5-nitro-3-vinylsalicylaldehyde, 389 mg (0.58 mmole) of 5-methoxy-2-methyl-3-octadecylbenzoselenazolium parachlorobenzenesulfonate and 12 ml of methanol, giving a homogeneous solution. To the solution obtained was added a solution of 55.4 mg (0.64 mmole) of piperidine in 3 ml of methanol, and the resulting mixture was refluxed with heating for 4 hours. Next, the liquid reaction mixture was cooled to room temperature and the precipitate obtained was separated by filtration and dried in a vacuum, giving 286 mg (yield: 75.7%) of 6'-nitro-5-methoxy-3-octadecyl-8'-vinylspiro[benzoselenazolin-2,2'(2'H )-1'-benzopyran] as a black powder.

IR (KBr) 1524, 1319 cm$^{-1}$ $^1$-NMR (CDCl$_3$); δ ppm 0.87 (t, 3H, CH$_3$), 1.24 (s, 28H,

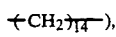

1.47 (m, 2H, —CH$_2$—), 1.91 (m, 2H, —CH$_2$—), 3.93 (s, 3H, CH$_3$O), 5.27 (dd, 1H, vinyl), 5.87 (dd, 1H, vinyl), 6.93 (d, 1H, vinyl), 7.06 (m, 2H, 4-H, 6-H), 7.60 (d, 1H, 4'-H), 7.79 (d, 1H, 7-H), 8.01 (d, 1H, 5'-H or 7'-H), 8.03 (d, 1H, 7'-H or 5'-H), 8.78 (bs, 1H, 3'-H)

The photochromic properties of the compound obtained above in Example 6 were determined. A solution of the compound in chloroform which was prepared by dissolving 30 mg of the compound per liter of chloroform was transparent deep blue at room temperature, and had an absorption maximum at 600 nm. When this solution was irradiated with visible rays for 1 minute with use of a 500-W ultra-high pressure mercury lamp equipped with a cut-off filter allowing passage of visible rays not shorter than 500 nm in wavelength, the initially observed absorption maximum peak disappeared and the solution became colorless and transparent. When maintained at 23° C., this solution assumed a blue color one minute later and turned deep blue again within a period of hour. The molecular absorption coefficient of the compound was $\epsilon = 27000$ at the maximum wavelength.

The foregoing solution was maintained at 0° C., irradiated with the same visible rays as above for 1 minute, giving a transparent, colorless solution. This solution was very stable at this temperature. When the colorless solution was irradiated with ultraviolet rays at 0° C. for 1 minute using a 500-W ultra-high pressure mercury lamp equipped with a cut-off filter allowing passage of ultraviolet rays having a wavelength of about 350 nm, the solution turned deep blue again. The solution was further subjected to a cycle repeatedly 100 times, one cycle consisting of color fading by means of visible light and coloration by means of ultraviolet light. During the 100 cycles, the absorbance of the solution in the colored state was never reduced, and the solution could be subjected to the cycle repeatedly with reproducibility.

The foregoing chloroform solution which was transparent deep blue at room temperature was irradiated with visible rays at 0° C. in the same manner as above, giving a transparent, colorless solution. This solution returned to its original transparent deep blue color when maintained at 25° C. for 30 minutes. In the case where this procedure was taken as one cycle, the solution could be subjected to the cycle repeatedly at least 30 times with reproducibility. During the cycles, the absorbance of the solution in the colored state was never reduced, and the solution was ready for being subjected to the cycle repeatedly many more times.

EXAMPLE 7

A 240 mg (0.6 mmole) quantity of 3,5-dimethyl-6'-nitro-8'-vinylspiro[benzoselenazolin-2,2'(2'H )-1'-benzopyran] obtained in Example 2 was dissolved in N,N-dimethylformamide which was distilled in a nitrogen stream. To the solution obtained was added 2.7 g (27 mmoles) of dry methyl methacrylate. As a polymerization initiator, 10 mg (0.06 mmole) of $\alpha,\alpha'$-azobisisobutyronitrile was added thereto to effect a polymerization reaction at 60° C. for 97 hours in a nitrogen atmosphere. The solution obtained by the reaction was added dropwise to 500 ml of methanol, whereby a purple solid was precipitated. The precipitate was isolated by centrifugation, dissolved in 40 ml of benzene and added dropwise to 500 ml of methanol again. The precipitate was collected by centrifugation and dried under reduced pressure, giving 312 mg of a purple powdery polymer.

From the following results obtained by the analysis, it was confirmed that the polymer obtained was a copolymer of the starting spiropyran compound of the formula (Ia) and methyl methacrylate. Stated more specifically, it was found, from the results of IR analysis, that the copolymer had absorptions (1542, 1400 cm$^{-1}$) due to a nitro group in addition to a strong absorption (1729 cm$^{-1}$) due to an ester carbonyl group. From the results determined by gel permeation chromatography (GPC) (solvent: tetrahydrofuran, temperature: 40° C., based on a standard polystyrene), it was revealed that the copolymer exhibited a substantially single peak and had a number average molecular weight $Mn = 1.10 \times 10^4$ and a weight average molecular weight $Mw = 1.25 \times 10^4$. The molecular absorption coefficient ($\epsilon$) of the starting spiropyran monomer in chloroform was 29,000 and that of the above polymer was 15,000. Assuming that each of the spiropyran units of the monomer and the polymer had the same molecular absorption coefficient in the above solvent, the content of the spiropyran unit of the formula (I) in the copolymer was 21 mole %.

A solution of 1.1 mg of the polymer in 50 ml of chloroform was transparent deep blue at room temperature, and had an absorption maximum at 599 nm. When the solution was irradiated with visible rays using a 500-W ultra-high pressure mercury lamp equipped with a cut-off filter allowing passage of visible rays not shorter than 500 nm in wavelength, the initially observed absorption maximum peak disappeared and the solution became colorless and transparent. This solution turned deep blue again when maintained at 25° C. for about 1 hour. FIG. 4 shows the visible light absorption spectrum determined at the time when the colored state reached equilibrium.

EXAMPLE 8

A 177 mg (0.29 mmole) quantity of 3,5-dimethyl-6'-nitro-8'-vinylspiro[benzoselenazolin-2,2'(2'H)-1'-benzopyran] was dissolved in 40 ml of N,N-dimethylformamide which was distilled in a nitrogen stream. To the solution was added 6.3 g (63.0 mmoles) of dry methyl methacrylate. A 37 mg (0.23 mmole) quantity of $\alpha,\alpha'$-azobisisobutyronitrile as a polymerization initiator was added thereto, and the resulting mixture was polymerized at 60° C. for 94 hours in a nitrogen atmosphere. The solution obtained by the reaction was added dropwise to 700 ml of methanol to precipitate a purple solid. The precipitate was isolated by centrifugation, dissolved in 40 ml of benzene and added dropwise to 500 ml of methanol again. The precipitate was collected by centrifugation and dried under reduced pressure, giving 3.20 g of a purple powdery polymer.

From the following results obtained by the analysis, it was confirmed that the polymer obtained was a copolymer of the starting spiropyran compound of the formula (Ia) and methyl methacrylate. More specifically, it was revealed, from the results of IR analysis, that the polymer had an absorption (1390 cm$^{-1}$) due to a nitro group in addition to a strong absorption (1730 cm$^{-1}$) due to an ester carbonyl group. Further, from the results determined by GPC, the polymer was found to exhibit a substantially single peak and to have a number average molecular weight $Mn = 3.0 \times 10^4$ and a weight average molecular weight $Mw = 5.7 \times 10^4$. The results of elementary analysis were C: 58.86%, H: 7.78% and N: 0.51%. From this result, it was revealed that the content of the spiropyran unit of the formula (I) in the copolymer was 0.02 mole %.

A 50 mg quantity of this polymer was dissolved in 1 ml of benzene and the solution was cast onto a quartz plate, giving a purple thin film. The film initially had an absorption maximum at 574 nm. When the film was irradiated with visible rays with use of a 500-W ultrahigh pressure mercury lamp equipped with a cut-off filter allowing passage of visible rays not shorter than 500 nm in wavelength, the previous absorption maximum peak disappeared and the film became colorless and transparent. This colorless film gradually assumed a purple color when maintained at room temperature (23° C.) However, the film did not become fully colored at room temperature but was stably fixed in and maintained a semi-uncolored state at an uncolored species fixation percentage of 54%.

Thus, upon ultraviolet irradiation, this film turned into the colored species, which upon visible light irradiation, again shifted to the colorless state (uncolored species) and, when allowed to stand at 23° C., maintained the semi-uncolored state at an uncolored species fixation percentage of 54%. This cycle could be repeated.

The "uncolored species fixation percentage" as so termed herein is defined as follows (the same shall apply in the subsequent examples):

Uncolored species fixation percentage (%) =

$$\frac{(\text{Maximum absorbance} - \text{Absorbance in fixed state})}{(\text{Maximum absorbance} - \text{Absorbance in uncolored state})} \times 100$$

In the above equation, the "absorbance in fixed state" means the absorbance at the absorption maximum wavelength in a state such that the increase in absorbance is substantially unobservable any more generally after the lapse of about 24 hours following visible light irradiation, although this period may vary depending on the sample to be tested. The "absorbance in uncolored state" means the absorbance at the above-mentioned absorption maximum wavelength immediately after visible light irradiation for fading.

EXAMPLE 9

A 103 mg (0.27 mmole) quantity of 3-methyl-6'-nitro-8'-vinylspiro[benzoselenazolin-2,2'(2'H)-1'-benzopyran] obtained in Example 1 was dissolved in 40 ml of N,N'-dimethylformamide which was distilled in a nitrogen stream. To the solution was added 5.8 g (58.0 mmoles) of dry methyl methacrylate. A 40 mg (0.24 mmole) quantity of α,α'-azobisisobutyronitrile was further added thereto and the resulting mixture was polymerized at 60° C. for 94 hours in a nitrogen atmosphere, followed by the same treatment as conducted in Example 8, giving 2.92 g of a purple powdery polymer.

From the following results determined by the analysis, it was confirmed that the obtained polymer was a copolymer of the spiropyran compound of the formula (Ia) and methyl methacrylate. Stated more specifically, the results of IR analysis showed that the polymer had an absorption (1390 cm$^{-1}$) due to a nitro group in addition to a strong absorption (1730 cm$^{-1}$) due to an ester carbonyl group. From the results determined by GPC, the polymer indicated a substantially single peak and was found to have a number average molecular weight Mn=$2.8 \times 10^4$ and a weight average molecular weight Mw=$4.5 \times 10^4$. The results of elementary analysis were C: 59.14%, H: 7.83% and N: 0.36%. From this result, it was revealed that the content of spiropyran unit of the formula (I) in the copolymer was 0.01 mole %.

A purple thin film was produced in the same manner as in Example 8. The film initially had an absorption maximum at 574 nm. When the film was irradiated with visible rays not shorter than 500 nm in wavelength in the same manner as in Example 8, the initially observed absorption maximum peak disappeared and the film became colorless and transparent. This colorless film gradually assumed a purple color at room temperature. However, the film did not become fully colored at this temperature but was stably fixed in and maintained a semi-uncolored state at an uncolored species fixation percentage of 47%. FIG. 5 shows visible light absorption spectra indicating this fact. Thus, upon ultraviolet irradiation, this film turned into the colored species, which, upon visible light irradiation, again shifted to the colorless state (uncolored species) and, when allowed to stand at 24° C., maintained the semi-uncolored state at an uncolored species fixation percentage of 47%. This cycle could be repeated.

EXAMPLE 10

The same procedure as in Example 9 was repeated with the exception of using 100 mg (0.24 mmole) of 5-methoxy-3-methyl-6'-nitro-8'-vinylspiro[benzoselenazolin-2,2'(2'H)-1'-benzopyran] obtained in Example 3, giving 1.81 g of a purple powdery polymer.

From the following results determined by the analysis, it was confirmed that the polymer obtained was a copolymer of the starting spiropyran compound of the formula (Ia) and methyl methacrylate. More specifically, the results determined by IR analysis showed that the polymer had an absorption (1389 cm$^{-1}$) due to a nitro group in addition to a strong absorption (1731 cm$^{-1}$) due to an ester carbonyl group. Further, the results determined by GPC revealed that the polymer exhibited a substantially single peak and had a number average molecular weight Mn=$2.6 \times 10^4$ and a weight average molecular weight Mw=$4.5 \times 10^4$. The results determined by elementary analysis were C: 58.85%, H: 7.74% and N: 0.45%. This result revealed that the content of spiropyran unit of the formula (I) in the copolymer was 0.02 mole %.

A purple thin film was produced from this polymer by the same manner as in Example 8. The film initially had an absorption maximum at 577 nm. When the film was irradiated with visible rays not shorter than 500 nm in wavelength in the same manner as in Example 8, the previous absorption maximum peak disappeared and the film became colorless and transparent. This colorless film gradually assumed a purple color at room temperature. However, the film did not become fully colored at this temperature but was stably fixed in and maintained a semi-uncolored state at an uncolored species fixation percentage of 65%. Thus, upon ultraviolet irradiation, this film turned into the colored species, which, upon visible light irradiation, again shifted to the colorless state (uncolored species) and, when allowed to stand at 24° C., maintained the semi-uncolored state at an uncolored species fixation percentage of 65%. This cycle could be repeated.

EXAMPLE 11

A 32 mg (0.049 mmole) quantity of 5-methoxy-6'-nitro-3-octadecyl-8'-vinylspiro[benzoselenazolin-2,2'(2'H)-1'-benzopyran] obtained in Example 6 was dissolved in 8 ml of anhydrous toluene. To the solution was added 1.0 g (10.0 mmoles) of dry methyl methacrylate and 6.9 mg (0.041 mmole) of α,α'-azobisisobutyronitrile. The resulting mixture was heated at 80° C. for 72 hours in a nitrogen atmosphere.

The reaction mixture was concentrated under reduced pressure to half of the initial quantity thereof and poured into 100 ml of methanol and the precipitate obtained was collected by centrifugation and dried, giving 151 mg of a light brown powdery polymer.

From the following results determined by the analysis, it was confirmed that the polymer obtained was a copolymer of the starting spiropyran compound of the formula (Ia) and methyl methacrylate. More specifically, the results determined by IR analysis revealed that the polymer had an absorption (1395 cm$^{-1}$) due to a nitro group and a strong absorption (1730 cm$^{-1}$) due to an ester carbonyl group. Further, the results determined by GPC showed that the polymer exhibited a substantially single peak and had a number average molecular weight $Mn=2.1\times 10^4$ and a weight average molecular weight $Mw=3.2\times 10^4$. The molar absorption coefficient of the starting spiropyran monomer in chloroform was 31000, and that of the above polymer was 5000. Assuming that each of the spiropyran units of the monomer and the polymer have the same molecular absorption coefficient in the above solvent, the content of the spiropyran unit of the formula (I) in the copolymer was 0.07 mole %.

A solution of 2.3 mg of the polymer in 10 ml of chloroform was transparent deep blue at room temperature and had an absorption maximum at 590 nm. When the solution was irradiated with visible rays not shorter than 500 nm in wavelength, the previous absorption maximum peak disappeared and the solution became colorless and transparent. When maintained at 25° C. for about 1 hour, this solution assumed a deep blue color again.

EXAMPLE 12

A 150 mg (0.36 mmole) quantity of 5-methoxy-3-methyl-6'-nitro-8'-vinylspiro[benzeselenazolin-2,2'(2'H)-1'-benzopyran] obtained in Example 3 was dissolved in 10 ml of N,N-dimethylformamide which was distilled in a nitrogen stream. To the solution was added 42 mg (0.25 mmole) of αα'-azobisisobutyronitrile, and the resulting mixture was polymerized at 80° C. for 72 hours. The solution obtained by the polymerization reaction was added dropwise to 250 ml of methanol, giving a purple precipitate. The precipitate was isolated by centrifugation and dried, giving 31 mg of a polymer.

The results of IR analysis revealed that an absorption (1590 cm$^{-}$') considered to be due to a vinyl group disappeared. The results determined by GPC showed that the polymer exhibited a single peak and had a number average molecular weight $Mn=1.60\times 10^3$ and a weight average molecular weight $Mw=1.97\times 10^3$. The results of elementary analysis were C: 54.71%, H: 3.98% and N: 7.01%. From the above results, it was confirmed that the foregoing polymer was a homopolymer of the starting spiropyran compound.

The solution of this polymer in DMF was purple at room temperature and initially had an absorption maximum at 568 nm. When the solution was irradiated with visible rays in the same manner as in Example 8, the initially observed absorption maximum disappeared and the solution became colorless. When allowed to stand at room temperature, this solution gradually assumed a purple color.

I claim:

1. A benzoselenazolino-vinylspiropyran compound of the formula

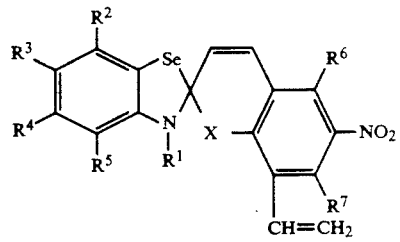

wherein $R^1$ is an alkyl group having 1 to 20 carbon atoms or a phenyl-$C_1$-$C_6$ alkyl group optionally substituted on phenyl by one to five substituents selected from the group consisting of $C_1$-$C_6$ alkyl group, $C_1$-$C_6$ alkoxy group, halogen atom, cyano group, trichloromethyl group, trifluoromethyl group and nitro group;

$R^2$, $R^3$, $R^4$ and $R^5$ are the same or different and each represents a hydrogen atom, an alkyl group having 1 to 6 carbon atoms, a phenyl group, a naphthyl group or a phenyl-$C_1$-$C_6$ alkyl group each optionally substituted by one to five of said substituents; an alkoxy group having 1 to 5 carbon atoms, a halogen atom, a cyano group, a trichloromethyl group, a trifluoromethyl group or a nitro group;

$R^6$ and $R^7$ are the same or different and each represents a hydrogen atom, an alkyl group having 1 to 6 carbon atoms, a phenyl group, a naphthyl group or a phenyl-$C_1$-$C_6$ alkyl group each optionally substituted by one to five or said substituents; a halogen atom, a cyano group or a nitro group;

and X is an oxygen atom or a sulfur atom.

2. A compound as defined in claim 1 wherein $R^1$ is an alkyl group having 1 to 20 carbon atoms; $R^2$, $R^3$, $R^4$ and $R^5$ are the same or different and each represents a hydrogen atom, a methyl group, an ethyl group, a phenyl group, a methoxy-phenyl group, a methoxy group, an ethoxy group, a fluorine atom, a chlorine atom, a bromine atom, a cyano group or a nitro group; $R^6$ and $R^7$ are the same or different and each represents a hydrogen atom, a methyl group, an ethyl group, a phenyl group or a naphthyl group; and X is an oxygen atom.

3. A compound as defined in claim 1 wherein $R^1$ is an alkyl group having 1 to 18 carbon atoms; $R^2$, $R^5$, $R^6$ and $R^7$ are hydrogen atoms; $R^3$ and $R^4$ are the same or different and each represents a hydrogen atom, an alkyl group having 1 to 6 carbon atoms or an alkoxy group having 1 to 5 carbon atoms; and X is an oxygen atom.

4. A compound as defined in claim 1 wherein $R^1$ is a methyl group or an octadecyl group; $R^2$, $R^3$, $R^5$, $R^6$ and $R^7$ are hydrogen atoms; $R^4$ is a hydrogen atom, a methyl group or a methoxy group; and X is an oxygen atom.

* * * * *